(12) United States Patent
Jacobsen et al.

(10) Patent No.: US 8,358,462 B2
(45) Date of Patent: *Jan. 22, 2013

(54) MINI-SCOPE FOR MULTI-DIRECTIONAL IMAGING

(76) Inventors: Stephen C. Jacobsen, Salt Lake City, UT (US); David Marceau, Salt Lake City, UT (US); Fraser Smith, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/946,442

(22) Filed: Nov. 15, 2010

(65) Prior Publication Data
US 2011/0286089 A1 Nov. 24, 2011

Related U.S. Application Data

(63) Continuation of application No. 11/810,702, filed on Jun. 5, 2007, now Pat. No. 7,835,074.

(51) Int. Cl.
*G02B 23/00* (2006.01)
*G02B 5/28* (2006.01)

(52) U.S. Cl. ......... 359/367; 359/399; 359/589; 359/634

(58) Field of Classification Search .................. 359/363, 359/367, 399–431, 618, 634, 483–502, 589
See application file for complete search history.

(56) References Cited

U.S. PATENT DOCUMENTS

| | | |
|---|---|---|
| 3,817,635 A | 6/1974 | Kawahara |
| 3,856,000 A | 12/1974 | Chikama |
| 3,886,933 A | 6/1975 | Mori et al. |
| 3,918,438 A | 11/1975 | Hayamizu et al. |
| 3,971,065 A | 7/1976 | Bayer |
| 4,277,168 A | 7/1981 | Oku |
| 4,283,115 A | 8/1981 | Fraissl |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |

(Continued)

FOREIGN PATENT DOCUMENTS

| | | |
|---|---|---|
| CN | 1481753 | 3/2004 |
| EP | 0482997 | 4/1992 |

(Continued)

OTHER PUBLICATIONS

Boppart, S.A. et al., "Forward-imaging instruments for optical coherence tomography." Optics Letters, Nov. 1, 1997, vol. 22, No. 21, pp. 1618-1620.

(Continued)

*Primary Examiner* — Thong Nguyen
(74) *Attorney, Agent, or Firm* — Thorpe North & Western LLP

(57) ABSTRACT

A mini-scope for multi-directional imaging is disclosed. The mini-scope includes an elongated mini-scoped body. An emissions aperture is disposed on the distal end of the elongated mini-scope body, which can be configured to emit a beam of optical energy propagating through a flexible optical conductor. A selective mirror is also positioned at the distal end of the elongated mini-scope body and is configured to selectively pass or reflect the beam of optical energy based on the optical characteristics of the beam. A solid state imaging device is further disposed on the distal end of the elongated mini-scope body for imaging illumination reflected by an external object in response to the beam of optical energy. This illumination is directed to pass through or reflect from the selective mirror to the camera based on optical characteristics of the beam.

16 Claims, 4 Drawing Sheets

U.S. PATENT DOCUMENTS

| | | |
|---|---|---|
| 4,585,349 A | 4/1986 | Gross et al. |
| 4,588,294 A | 5/1986 | Siegmund |
| 4,593,313 A | 6/1986 | Nagasaki et al. |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,641,927 A | 2/1987 | Prescott et al. |
| 4,646,724 A | 3/1987 | Sato et al. |
| 4,706,118 A | 11/1987 | Kato et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takhashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,639 A | 6/1992 | Srivastava |
| 5,130,804 A | 7/1992 | Tamura et al. |
| 5,165,063 A | 11/1992 | Strater et al. |
| 5,166,656 A | 11/1992 | Badehi et al. |
| 5,182,672 A | 1/1993 | Mukai et al. |
| 5,188,093 A | 2/1993 | Lafferty et al. |
| 5,191,203 A | 3/1993 | McKinley |
| 5,198,894 A | 3/1993 | Hicks |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljic et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna |
| 5,547,906 A | 8/1996 | Badehi |
| 5,594,497 A | 1/1997 | Ahern |
| 5,603,687 A | 2/1997 | Hori et al. |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,142,930 A | 11/2000 | Ito et al. |
| 6,161,035 A | 12/2000 | Furusawa |
| 6,184,923 B1 | 2/2001 | Miyazaki |

| | | | | | | |
|---|---|---|---|---|---|---|
| 6,211,955 B1 | 4/2001 | Basiji et al. | | 7,591,780 B2 | 9/2009 | Jacobsen |
| 6,261,226 B1 | 7/2001 | McKenna et al. | | 7,629,659 B2 | 12/2009 | Jacobsen |
| 6,262,855 B1 | 7/2001 | Greisz | | 7,787,939 B2 | 8/2010 | Jacobsen et al. |
| 6,288,172 B1 | 9/2001 | Goetz et al. | | 7,823,215 B2 | 10/2010 | Giakos |
| 6,319,745 B1 | 11/2001 | Bertin et al. | | 7,835,074 B2 * | 11/2010 | Jacobsen et al. .............. 359/367 |
| 6,322,498 B1 | 11/2001 | Gravenstein et al. | | 7,901,870 B1 | 3/2011 | Wach |
| 6,327,096 B1 | 12/2001 | Tsuchida | | 2001/0007051 A1 | 7/2001 | Nakashima |
| 6,352,503 B1 | 3/2002 | Matsue | | 2001/0007511 A1 | 7/2001 | Minami et al. |
| 6,361,491 B1 | 3/2002 | Hasegawa et al. | | 2001/0024848 A1 | 9/2001 | Nakamura |
| 6,366,726 B1 | 4/2002 | Wach et al. | | 2001/0049509 A1 | 12/2001 | Sekine et al. |
| 6,384,397 B1 | 5/2002 | Takiar et al. | | 2002/0007110 A1 | 1/2002 | Irion |
| 6,384,884 B1 | 5/2002 | Nakamura et al. | | 2002/0080248 A1 | 6/2002 | Adair et al. |
| 6,396,116 B1 | 5/2002 | Kelly et al. | | 2002/0109774 A1 | 8/2002 | Meron et al. |
| 6,445,939 B1 | 9/2002 | Swanson et al. | | 2002/0111534 A1 | 8/2002 | Suzuki et al. |
| 6,456,423 B1 | 9/2002 | Nayfeh et al. | | 2002/0166946 A1 | 11/2002 | Iizuka et al. |
| 6,471,636 B1 * | 10/2002 | Sano et al. .................... 600/109 | | 2002/0188204 A1 | 12/2002 | McNamara |
| 6,485,413 B1 | 11/2002 | Boppart et al. | | 2002/0193660 A1 | 12/2002 | Weber |
| 6,522,913 B2 | 2/2003 | Swanson et al. | | 2003/0071342 A1 | 4/2003 | Honda et al. |
| 6,533,722 B2 | 3/2003 | Nakashima | | 2003/0092995 A1 | 5/2003 | Thompson |
| 6,537,205 B1 | 3/2003 | Smith | | 2003/0197812 A1 | 10/2003 | Hirata et al. |
| 6,552,796 B2 | 4/2003 | Magnin et al. | | 2003/0199761 A1 | 10/2003 | Yock |
| 6,561,972 B2 | 5/2003 | Ooshima et al. | | 2003/0202127 A1 | 10/2003 | Hirata et al. |
| 6,570,659 B2 | 5/2003 | Schmitt | | 2003/0220574 A1 | 11/2003 | Markus et al. |
| 6,573,950 B1 | 6/2003 | Hirata et al. | | 2003/0222325 A1 | 12/2003 | Jacobsen et al. |
| 6,585,717 B1 | 7/2003 | Wittenberg et al. | | 2004/0017961 A1 | 1/2004 | Petersen et al. |
| 6,595,913 B2 | 7/2003 | Takahashi | | 2004/0059204 A1 | 3/2004 | Marshall |
| 6,618,614 B1 | 9/2003 | Chance et al. | | 2004/0097804 A1 | 5/2004 | Sobe |
| 6,622,367 B1 | 9/2003 | Bolduc et al. | | 2004/0181148 A1 | 9/2004 | Uchiyama et al. |
| 6,643,071 B2 | 11/2003 | Schnitzer | | 2004/0225222 A1 | 11/2004 | Zeng et al. |
| 6,658,279 B2 | 12/2003 | Swanson et al. | | 2005/0054902 A1 | 3/2005 | Konno |
| 6,695,787 B2 | 2/2004 | Hogendijk et al. | | 2005/0065504 A1 | 3/2005 | Melsky et al. |
| 6,719,686 B2 | 4/2004 | Coakley et al. | | 2005/0088576 A1 | 4/2005 | Hirata et al. |
| 6,727,313 B2 | 4/2004 | Zhou et al. | | 2005/0124875 A1 | 6/2005 | Kawano et al. |
| 6,761,684 B1 | 7/2004 | Speier | | 2005/0152421 A1 | 7/2005 | Fujitani |
| 6,785,048 B2 | 8/2004 | Yamaguchi et al. | | 2005/0154277 A1 | 7/2005 | Tang et al. |
| 6,826,422 B1 | 11/2004 | Modell et al. | | 2005/0158899 A1 | 7/2005 | Jacobsen et al. |
| 6,827,683 B2 | 12/2004 | Otawara | | 2005/0174649 A1 | 8/2005 | Okada et al. |
| 6,833,916 B2 | 12/2004 | Osipchuk et al. | | 2005/0187568 A1 | 8/2005 | Klenk et al. |
| 6,834,158 B1 | 12/2004 | Templeton | | 2005/0197534 A1 | 9/2005 | Barbato et al. |
| 6,842,288 B1 | 1/2005 | Liu et al. | | 2005/0231718 A1 | 10/2005 | Goodall et al. |
| 6,850,659 B2 | 2/2005 | Han | | 2005/0234345 A1 | 10/2005 | Yang |
| 6,879,851 B2 | 4/2005 | McNamara et al. | | 2005/0264813 A1 | 12/2005 | Giakos |
| 6,881,448 B1 | 4/2005 | Hattori | | 2005/0267340 A1 | 12/2005 | Ishihara et al. |
| 6,891,984 B2 | 5/2005 | Petersen et al. | | 2005/0288555 A1 | 12/2005 | Binmoeller |
| 6,894,729 B2 | 5/2005 | Hirata et al. | | 2006/0009682 A1 | 1/2006 | Nagasawa et al. |
| 6,898,458 B2 | 5/2005 | Zeng et al. | | 2006/0013593 A1 | 1/2006 | Yokoo et al. |
| 6,900,913 B2 | 5/2005 | Chen | | 2006/0017928 A1 | 1/2006 | Crowther |
| 6,930,705 B2 * | 8/2005 | Tanaka ........................ 348/45 | | 2006/0069312 A1 | 3/2006 | O.Connor |
| 6,937,268 B2 | 8/2005 | Ogawa | | 2006/0079835 A1 | 4/2006 | Frassica |
| 6,939,348 B2 | 9/2005 | Malecki et al. | | 2006/0146172 A1 | 7/2006 | Jacobsen et al. |
| 6,941,041 B2 | 9/2005 | Yamaguchi et al. | | 2006/0252994 A1 | 11/2006 | Ratnakar |
| 6,944,204 B2 | 9/2005 | Zhou et al. | | 2006/0253088 A1 | 11/2006 | Chow et al. |
| 6,953,432 B2 | 10/2005 | Schiefer | | 2007/0010709 A1 | 1/2007 | Reinschke |
| 6,956,624 B2 | 10/2005 | Hirata et al. | | 2007/0032796 A1 | 2/2007 | Chin-Chen et al. |
| 6,960,165 B2 | 11/2005 | Ueno et al. | | 2007/0073321 A1 | 3/2007 | Mikkaichi et al. |
| 6,982,740 B2 | 1/2006 | Adair et al. | | 2007/0083232 A1 | 4/2007 | Lee |
| 6,990,271 B2 | 1/2006 | Gafsi et al. | | 2007/0135803 A1 | 6/2007 | Belson |
| 7,030,904 B2 | 4/2006 | Adair et al. | | 2007/0208252 A1 | 9/2007 | Makower |
| 7,033,317 B2 | 4/2006 | Pruitt | | 2007/0233187 A1 | 10/2007 | Lobello |
| 7,058,294 B2 | 6/2006 | Nakahara | | 2007/0239066 A1 | 10/2007 | Laham et al. |
| 7,075,576 B2 | 7/2006 | Creasey et al. | | 2007/0255392 A1 | 11/2007 | Johnson |
| 7,081,927 B2 | 7/2006 | Hirata et al. | | 2007/0293727 A1 | 12/2007 | Goldfarb et al. |
| 7,091,500 B2 | 8/2006 | Schnitzer | | 2008/0045794 A1 | 2/2008 | Belson |
| 7,098,871 B1 | 8/2006 | Tegreene et al. | | 2008/0177141 A1 | 7/2008 | Wu et al. |
| 7,108,657 B2 | 9/2006 | Irion et al. | | 2008/0183080 A1 | 7/2008 | Abraham |
| 7,153,299 B1 | 12/2006 | Tu et al. | | 2008/0188767 A1 | 8/2008 | Oaki et al. |
| 7,165,552 B2 | 1/2007 | Deem et al. | | 2009/0027765 A1 | 1/2009 | Kamijima |
| 7,166,537 B2 | 1/2007 | Jacobsen et al. | | 2009/0036764 A1 | 2/2009 | Rivas et al. |
| 7,167,317 B2 | 1/2007 | Jung et al. | | 2009/0054791 A1 | 2/2009 | Flusberg |
| 7,186,251 B2 | 3/2007 | Malecki et al. | | 2009/0082626 A1 | 3/2009 | Ichimura et al. |
| 7,218,822 B2 | 5/2007 | Treado et al. | | 2009/0119808 A1 | 5/2009 | Giakos |
| 7,221,388 B2 | 5/2007 | Sudo et al. | | 2009/0137928 A1 | 5/2009 | Quick et al. |
| 7,234,816 B2 | 6/2007 | Bruzzone et al. | | 2009/0143645 A1 | 6/2009 | Matthes |
| 7,247,847 B2 | 7/2007 | Webb et al. | | 2009/0156899 A1 | 6/2009 | Konishi |
| 7,304,310 B1 | 12/2007 | Shortt et al. | | 2009/0180197 A1 | 7/2009 | Jacobsen et al. |
| 7,393,321 B2 | 7/2008 | Doguchi et al. | | 2009/0234325 A1 | 9/2009 | Rozenberg et al. |
| 7,420,675 B2 | 9/2008 | Giakos | | 2009/0287048 A1 | 11/2009 | Jacobson et al. |
| 7,511,891 B2 | 3/2009 | Messerschmidt | | | | |
| 7,554,597 B2 | 6/2009 | Scherling | | | | |

| | | |
|---|---|---|
| 2010/0085567 A1 | 4/2010 | Dottery et al. |
| 2010/0171821 A1 | 7/2010 | Jacobsen et al. |
| 2010/0248178 A1 | 9/2010 | Nahlieli |

FOREIGN PATENT DOCUMENTS

| | | |
|---|---|---|
| EP | 0550 995 | 7/1993 |
| EP | 0639043 | 2/1995 |
| EP | 0681809 | 11/1995 |
| EP | 1104182 | 5/2001 |
| EP | 1477104 | 11/2004 |
| EP | 1626436 | 2/2006 |
| JP | 63-155115 | 6/1988 |
| JP | 5 -049602 | 3/1993 |
| JP | 08-076028 | 3/1996 |
| JP | 08084700 | 4/1996 |
| JP | 11 137512 | 5/1999 |
| JP | 2001/314365 | 11/2001 |
| JP | 2004/329700 | 11/2004 |
| JP | 2005334462 | 8/2005 |
| JP | 2006/162418 | 6/2006 |
| JP | 2007/312290 | 11/2007 |
| JP | 2009/067946 | 4/2009 |
| WO | WO98/38907 | 9/1998 |
| WO | WO99/40624 | 8/1999 |
| WO | WO00/54033 | 9/2000 |
| WO | WO 03/081831 | 10/2003 |
| WO | WO2006/060777 | 6/2006 |
| WO | WO 2007/138889 | 12/2007 |

OTHER PUBLICATIONS

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

http://news.thomasnet.com/fullstory/23462, "Near-IR Camera Utilizes CCD Array with Phosphor Coating"; Jun. 11, 2003; 5 pages.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 11/810,702, filed Jun. 5, 2007.

Jacobsen, Stephen C., U.S. Appl. No. 12/008,486, filed Jan. 11, 2008.

Jacobsen, Stephen C., U.S. Appl. No. 12/079,741, filed Mar. 27, 2008.

Jacobsen, Stephen C., U.S. Appl. No. 12/152,730, filed May 16, 2008.

Jacobsen, Stephen C., U.S. Appl. No. 12/487,481, filed Jun. 18, 2009.

Jacobsen, Stephen C., U.S. Appl. No. 12/487,495, filed Jun. 18, 2009.

Jacobsen, Stephen C., U.S. Appl. No. 12/512,188, filed Jul. 30, 2009.

Jacobsen, Stephen C.; U.S. Appl. No. 12/611,776, filed Nov. 3, 2009.

Jacobsen, Stephen C.; U.S. Appl. 12/792,562, filed Jun. 2, 2010.

Jacobsen, Stephen C.; U.S. Appl. No. 12/896,731, filed Oct. 1, 2010.

Jacobsen, Stephen C.; U.S. Appl. No. 12/896,732, filed Oct. 1, 2010.

Jacobsen, Stephen C.; U.S. Appl. No. 12/896,737, filed Oct. 1, 2010.

Jacobsen, Stephen C.; U.S. Appl. No. 12/896,743, filed Oct. 1, 2010.

Jacobsen, Stephen C.; U.S. Appl. No. 12/938,672, filed Nov. 3, 2010.

Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.

Literature from Grin Tech, "In vivo medical confocal imaging and optical coherence tomography," www.grintech.de, Revision Jun. 2001, pp. 1-3.

Microcam, MINAST Project 5.04, Nov. 11, 1999, http://www.imt.unine.ch/ESPLAB/www/projects/Microcam/, pp. 1-16.

Nguyen, Clark, "Communications Applications of Microelectromechanical Systems," Proceedings, Sensors Expo, May 19-21, 1998, San Jose, CA. pp. 447-455.

Tearney, G.J. et al., "Scanning single-mode fiber optic catheter-endoscope for otpical coherence tomography," Optics Letters, Apr. 1, 1996, vol. 21, No. 7, pp. 543-545.

Zeis, Michael et al., "Color Business Report," ISSN 1055-3339. Jul. 2002, p. 5.

Gaoping et al.; Research on the Measurement of Grin Lens Focused Spot Diameter and Resolution; Applied Optics; 1995; vol. 16, No. 6.

PCT Application PCT/US2010/051200; filed Oct. 1, 2010; Stephen C. Jacobsen; ISR mailed Jun. 3, 2011.

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

PCT Application PCT/US2010/051188; filed Oct. 1, 2010; Stephen C. Jacobsen; International Search Report mailed Jul. 13, 2011.

Xie et al; GRIN Lens Rod Based Probe for Endoscopic Spectral Domain Optical Coherence Tomography with Fast Dynamic Focus Tracking; Optics Express; Apr. 17, 2009; 9 pages; vol. 14, No. 8.

U.S. Appl. No. 12/152,730, filed May 16, 2008; Stephen C. Jacobson; office action issued Sep. 16, 2011.

\* cited by examiner

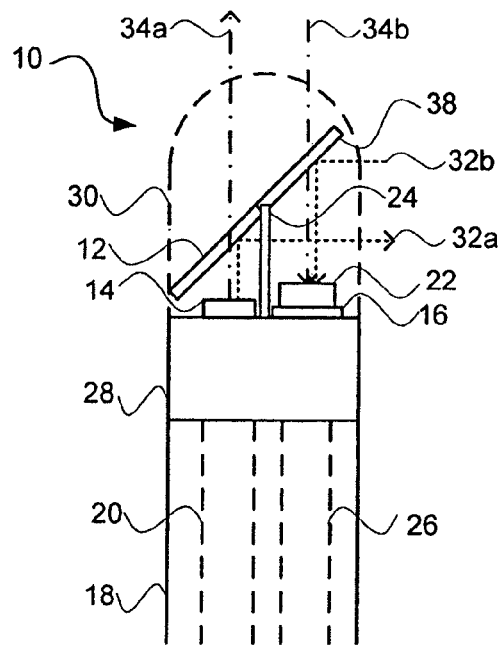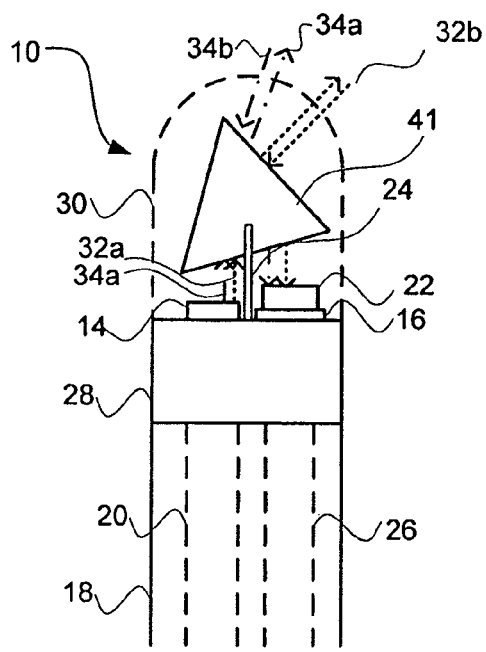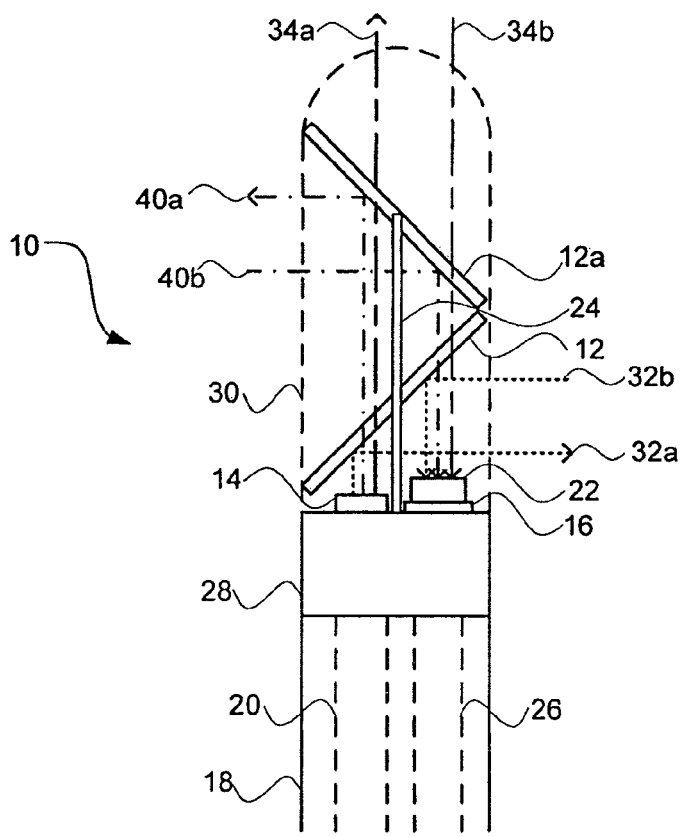

MINI-SCOPE FOR MULTI-DIRECTIONAL IMAGING

PRIORITY CLAIM

This application is a continuation application of U.S. patent application Ser. No. 11/810,702 filed on Jun. 5, 2007, now U.S. Pat. No. 7,835,074, which is incorporated herein by reference in its entirety.

SUMMARY

Briefly, and in general terms, the invention is directed to a mini-scope for multi-directional imaging. In one embodiment, the mini-scope includes an elongated mini-scope body having a flexible optical conductor. The flexible optical conductor has a distal and a proximal end. An emissions aperture is disposed on the distal end of the elongated mini-scope body to emit a beam of optical energy propagating through the flexible optical conductor. A selective mirror is also disposed at the distal end of the elongated mini-scope body. The selective mirror is configured to selectively pass and/or reflect the beam of optical energy based on the optical characteristics of the beam of optical energy. An SSID is also disposed at the distal end of the elongated mini-scope body for imaging illumination reflected by an external object in response to the beam of optical energy, the illumination is directed to pass through or reflect from the selective mirror to the camera based on optical characteristics of the beam.

BRIEF DESCRIPTION OF THE DRAWINGS

FIG. 3 is a side view of a mini-scope emitting and imaging multiple beams of optical energy, in accordance with another embodiment of the present invention;

FIG. 4 is a side view of a mini-scope having a prism member, in accordance with another embodiment of the present invention;

FIG. 5 is a side view of a mini-scope having a plurality of selective mirrors, in accordance with another embodiment of the present invention;

Figure 1:
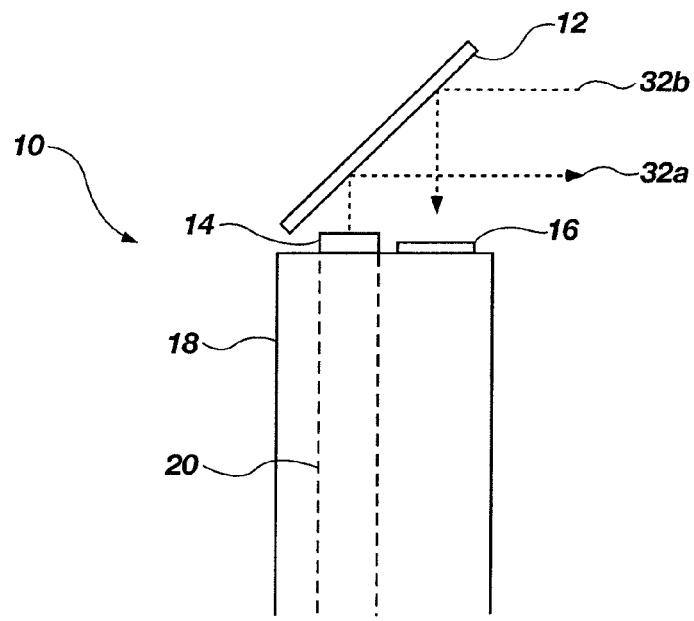
FIG. 1 is a side view of a mini-scope in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The following detailed description of exemplary embodiments of the invention makes reference to the accompanying drawings, which form a part hereof, and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention, as represented in FIGS. 1 through 7, is not intended to limit the scope of the invention, as claimed, but is presented for purposes of illustration and to sufficiently enable one skilled in the art to practice the invention. Accordingly, the scope of the present invention is to be defined solely by the appended claims.

The following detailed description and exemplary embodiments of the invention will be best understood by referencing the accompanying drawings, wherein the elements and features of the invention are designated by numerals throughout.

In describing and claiming the present invention, the following terminology will be used:

The singular forms "a," "an," and "the" include plural referents unless the context clearly dictates otherwise. Thus, for example, reference to "a beam of optical energy" includes reference to one or more of such beams, and reference to "an emitter" includes reference to one or more of such emitters.

As used herein, "mini-scope" refers to a miniature optical instrument for examining the inner parts of the body as well as for other optical applications.

As used herein, "SSID," Solid State Imaging Device, refers to a camera or imaging device having a size approximately equal to or less than the diameter of a bundle of optical fibers. SSIDs include, for example, charge-injection devices (CID), charge-coupled devices (CCD), complementary metal oxide semiconductor (CMOS) devices, and other miniature-sized imaging devices, including those made from compound semiconductors such as InGaAs, capable of imaging reflected illumination of visible and/or non-visible light.

As used herein, "selective mirror" refers to a surface, having selective reflection properties, based on various characteristics of the incident optical energy. These characteristics can include, for example: wavelength, polarization, intensity, direction, angle, frequency, and other like characteristics. The surface can be planar or nonplanar as suits a particular configuration.

As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range were explicitly recited.

As an illustration, a numerical range of "about 1 micrometer to about 5 micrometers" should be interpreted to include not only the explicitly recited values of about 1 micrometer to about 5 micrometers, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value and should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error, and the like, and other factors known to those of skill in the art.

Method steps, as described herein, can be performed without regard to order, unless specifically stated.

As illustrated in FIG. 1, a mini-scope 10, in accordance with one embodiment of the invention, includes a means for optically conducting a beam of optical energy. This means for optically conducting can include an elongated mini-scope body 18 having a flexible optical conductor 20, a single optical fiber having a jacket, and the like. The flexible optical conductor can be a flexible optical fiber having a substantially small diameter and being configured to transmit optical energy from one end of the mini-scope 10 to an opposite end. The elongated mini-scope body has, for example, a distal end and a proximal end, and a length of approximately 0.1 m to 3 m, with 0.5 m being an exemplary length, and a diameter of approximately 0.5 mm to 5 mm, with 1 mm being an exemplary diameter. In another aspect, a mini-scope 10, includes a source of optical energy (no shown) disposed on a distal end of the mini-scope 10 for generating a beam of optical energy at the distal end of the mini-scope 10.

This elongated mini-scope body is configured to be inserted into or in contact with a patient or device. The mini-scope can further include a means for emitting a beam of optical energy, such as an emissions aperture 14, an emissions aperture with a lens, or the like. An emissions aperture can be disposed on the distal end of the elongated mini-scope body for emitting the beam of optical energy propagating through the flexible optical conductor. A means for selectively directing a beam of optical energy can be positioned above the emissions aperture to selectively pass and reflect the beam of optical energy 32a based on the optical characteristics of the beam, as described in greater detail below. A means for imaging can also be disposed on the distal end of the elongated mini-scope body. This means for imaging can include a SSID 16, such as a mini charge coupled device (CCD) camera, a mini CMOS camera, or another optical energy detector designed to operate at other wavelengths. The means for imaging can image the illumination reflected by an external object in response to the beam of optical energy 32b, wherein the illumination is directed to pass through or reflect from the selective mirror to the means for imaging.

A means for selectively directing the beam of optical energy can selectively direct a beam or multiple beams of optical energy based on various optical characteristics of the beam. This means for selectively directing can include a selective mirror 12. For example, the selective mirror can be a dichroic mirror, a polarization dependant beam splitting plate, a polarization dependant beam splitting cube, a prism, a diffraction grating, or other optical devices that can be configured to selectively pass and reflect a beam or portion of a beam of optical energy based on the properties of the optical energy. In this way, the mini-scope 10 can provide both a forward and a lateral image to a user, without the need for turning, rotating, or redirecting the scope head and without substantially increasing the size of the scope.

As a particular exemplary embodiment, the selective mirror 12 can be a dichroic mirror or a mirror which reflects or passes a beam of optical energy based on the frequency characteristics of the beam of optical energy. Dichroic mirrors can be designed to reflect a specific wavelength region of optical energy. For example, a dichroic mirror can be designed to reflect blue light (e.g., light with an optical wavelength of about 440-550 nm), but pass red light (e.g., light with an optical wavelength of about 625-740 nm). As another example, a mirror can be designed to reflect all light having a wavelength of about 450±10 nm, thus reflecting most blue light, while passing light with an optical frequency outside of this range. Similarly, a dichroic mirror can be designed to pass and reflect other frequency regions, such as red light, or all near ultraviolet wavelength of about 380-200 nm.

In another embodiment of the invention, the selective mirror 12 can be a polarizing beam splitter cube or other optical element configured to pass or reflect a beam of optical energy based on the polarization characteristics of the beam. Typically, polarization beam splitter plates are designed to separate optical energy into the P- and S-components by passing one component and reflecting the other. This type of selective mirror can pass or reflect a spectrum of light frequencies, given constant P- or S-polarization.

The width of the selective mirror can be approximately the diameter of the elongated mini-scope body, and the length can vary according to the desired angular orientation of the mirror. This selective mirror can have a variety of shapes including an ellipse, a circle, a square, a rectangle, and the like. The selective mirror can be positioned at a fixed or movable angle. For example, this angle can be a 45 degree, 15 degree angle, facing in the reverse direction, or any other angular orientations relative to the plane of the supportive end structure 28, according to the design, usage, and type of the selective mirror.

Figure 2A:
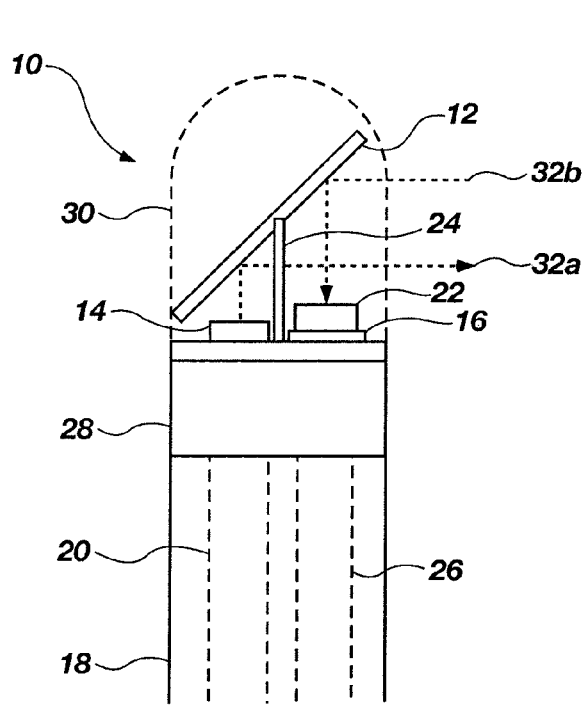
FIG. 2a-2b is a side view of a mini-scope in accordance with another embodiment of the present invention.
Figure 2B:
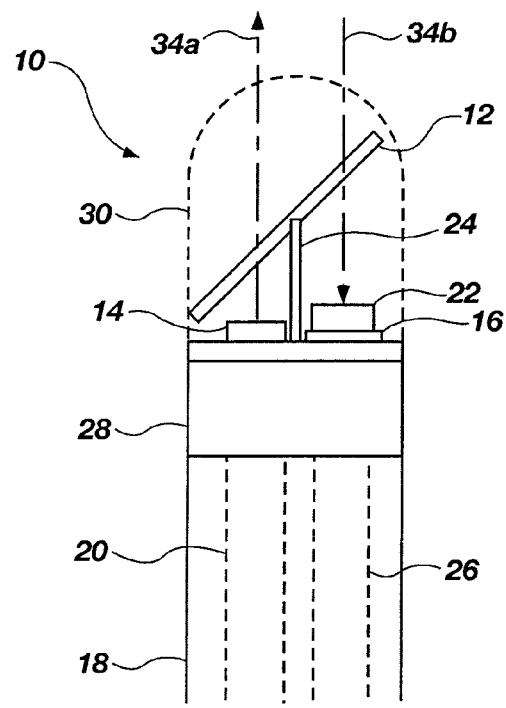

As illustrated in FIGS. 2a and 2b in accordance with another embodiment of the invention, a mini-scope 10, similar to that of FIG. 1, further includes a SSID 16, such as a charged coupled device (CCD) camera, having a gradient refractive index (GRIN) lens 22. The SSID is configured to transmit recorded images to a processing system (not shown) via an electrical connection 26, disposed within the elongated mini-scope body 18. In another aspect, the images could be sent via a wireless connection to a processing system. The elongated mini-scope body can further include a supportive end structure 28, disposed at its distal end. This supportive end structure can position the emissions aperture 14 and the SSID 16 in a forward direction. This structure can further be coupled to a mirror supporting structure 24, which holds the selective mirror 12 in position. The mirror supporting structure can be configured to support and control the structure in a fixed or movable position, according to a variety of suitable structural configurations and embodiments.

According to another embodiment of the present invention, the mini-scope 10 can include a rotating device (not shown) for rotating the selective mirror 12. The rotating device can be coupled to the supportive end structure and be configured to both support, rotate and/or pivot the selective mirror, the emissions aperture 14, and/or the SSID 16 about the center axis of the elongated mini-scope body 18. The rotating device can also rotate the supportive end structure and/or the selective mirror in other directions, as desired. Alternatively, the supportive end structure 28 and mirror supporting structure 24 can include rotational means. For example, a mirror supporting structure that serves as a rotating device can rotate the mirror so as to increase or decrease the direction of reflection. This mirror supporting structure can be made of a piezoelectric material that is configured to rotate the mirror in response to a predefined electrical condition. The rotating device can also rotate via a variety of other rotational means, including a mechanical device, electromechanical device, electromagnetic device, or other suitable device. Power for this device can be supplied through the electrical connection 26, or through a similar connection.

The mini-scope can also include a transparent shield 30, for protecting the patient and mini-scope elements. The shield may be coupled to the supportive end structure 28 and can be fabricated from various materials such as plastics, glass, ceramics, etc.

As illustrated in FIG. 2a, a first beam of optical energy 32a can be transmitted down the flexible optical conductor 20 and emitted towards the selective mirror 12, via the emissions aperture 14. Upon incidence with the selective mirror, the first beam can be reflected in a lateral direction, based on the optical characteristics of the first beam. According to one embodiment of the invention, the selective mirror can be a dichroic mirror, as described above. The dichroic mirror can be positioned at a 45 degree angle relative to the emissions apertures and can be configured to reflect all light having a wavelength of approximately 450±10 nm (blue light). By way of example, the first beam 32a has a wavelength of approximately 450 nm, the beam can be reflected by the dichroic mirror in a lateral direction, based on the optical characteristics of the first beam, as shown. The illumination 32b reflected by an external object (not shown) in a reverse-lateral direction, in response to the first beam of optical energy 32a, can also be directed by the selective mirror to the SSID. The external object is subsequently imaged by the SSID.

Alternatively, as illustrated in FIG. 2b, if a second beam of optical energy 34a, having a wavelength outside of the range 450±10 nm (e.g., approximately 650 nm), is transmitted down the flexible optical conductor 20 towards the same dichroic mirror, the second beam can be passed through the dichroic mirror in the forward direction based on the frequency properties of the second beam. The illumination 34b reflected by an external object (not shown) in a reverse direction, in response to the beam of optical energy 34a, can also pass through the selective mirror to the SSID. The external object is then imaged by the camera or other means for imaging.

Referring now to FIG. 3, according to another embodiment of the present invention, a first beam of optical energy 32a and a second beam of optical energy 34a can be simultaneously transmitted down a flexible optical conductor 20, wherein the first and second beams form first and second portions of a single beam of optical energy. In this manner, a first portion of the beam of optical energy can be passed through the selective mirror in a forward direction, while a second portion of the beam of optical energy can be concurrently reflected in a lateral direction. Similarly, the illumination reflected by an external object in a reverse direction, in response to the first portion of the beam, can be passed through the selective mirror to the imaging device 16 to produce a first recorded image. Whereas, the illumination reflected by an external object in a reverse-lateral direction, in response to the second portion of the beam of optical energy can be reflected by the selective mirror to the imaging device, to concurrently produce a second recorded image.

According to another embodiment of the invention, the selective mirror 12 of FIGS. 2a and 2b can be a polarizing beam splitter plate. The flexible optical conductor 20 can be a polarization maintaining optical fiber to maintain the polarization of a transmitted beam of optical energy. The polarizing beam splitter plate can function similarly to that of the dichroic mirror described above, passing P-polarized beams of optical energy and reflecting S-polarized beams of optical energy, or vice a versa, according to the type and orientation of the polarizing beam splitter. In one aspect of the invention, the function of the polarization beam splitter plate will differ from the function of the dichroic mirror in that the polarization beam splitter plate will primarily direct illumination reflected by an external object in response to the first or second beam of optical energy that is S-polarized or P-polarized, respectively. In the case that illumination reflected by an external object changes polarization, the polarization beam splitter plate will mostly misdirect this illumination away from the means for imaging or SSID 16.

To decrease the loss of the reflected illumination that has changed polarity, the selective mirror 12 can further include a non-selective portion, such as a half silvered mirror portion 38, as shown in FIG. 3. The half silvered mirrors reflect half of the incident light and transmit the other half so half of the illuminating light is incident on the SSID array.

According to another embodiment of the present invention, the means for selectively directing a beam of optical energy can be a prism 41, as illustrated in FIG. 4. The beam of optical energy can include multiple portions, such as frequency portions, including a first beam portion 32a and second beam portion 34a. The prism can selectively direct the beam portions, based on their respective optical characteristics. The reflected illumination of the first and second beam portions (32b and 34b respectively) can be further selectively directed by the prism to the SSID 16 for imaging to produce a recorded image. The recorded image can later be filtered and processed in order to separate the reflected illumination beam portions for display, as will be described below.

As illustrated in FIG. 5, in another embodiment, the mini-scope 10 can include a plurality of selective mirrors. By using a plurality of mirrors, the mini-scope can be configured to image multiple directions without the need for rotating the mini-scope device. Two or more cameras can be used according to the selective qualities and ranges of the selective mirrors. Each of the selective mirrors can be configured to selectively pass or reflect the beam of optical energy, based on optical characteristics of the beam. The mini-scope 10 can include a first selective mirror 12 and a second selective mirror 12a. This second selective mirror can have a different directional orientation to reflect a beam of optical energy in a second direction, based on the optical characteristics of the beam. The mirror supporting structure 24 can extend from the first selective mirror to the second selective mirror 12a to control both the positioning and directional orientation of the selective mirrors. Alternatively, a second mirror supporting structure can be included.

According to one embodiment of the present invention, the first and second selective mirrors 12 and 12a can be dichroic mirrors, positioned at 45 degrees and 135 degrees, respectively, relative to the emissions aperture. The first selective mirror 12 is configured to reflect optical energy having a wavelength of approximately 450±10 nm, while the second selective mirror is configured to reflect optical energy having a wavelength of approximately 550±10 nm. In order to obtain multi-directional images, a first beam of optical energy 32a, having a wavelength of 450 nm, can be transmitted down the flexible optical conductor. This first beam can be reflected by the first selective mirror, illuminating objects in the lateral direction. Simultaneously or alternatively, a second beam of optical energy 34a, having a wavelength of 550 nm can be transmitted down the flexible optical conductor. This second beam can pass through the first selective mirror and be reflected off the second selective mirror, illuminating objects in a reverse-lateral direction. Further, a third beam of optical energy 40a, having a wavelength of 650 nm (red light) can be either simultaneously or alternatively transmitted down the flexible optical conductor. This third beam can pass through the first and second selective mirrors, illuminating objects in a forward direction. The reflected illumination of the first, second, and third beams 32b, 34b, and 40b, in response to external objects are passed through or reflected from the first, second or both the first and second selective mirrors, towards the GRIN lens 22 and SSID 16 for producing a recorded image.

Figure 6:
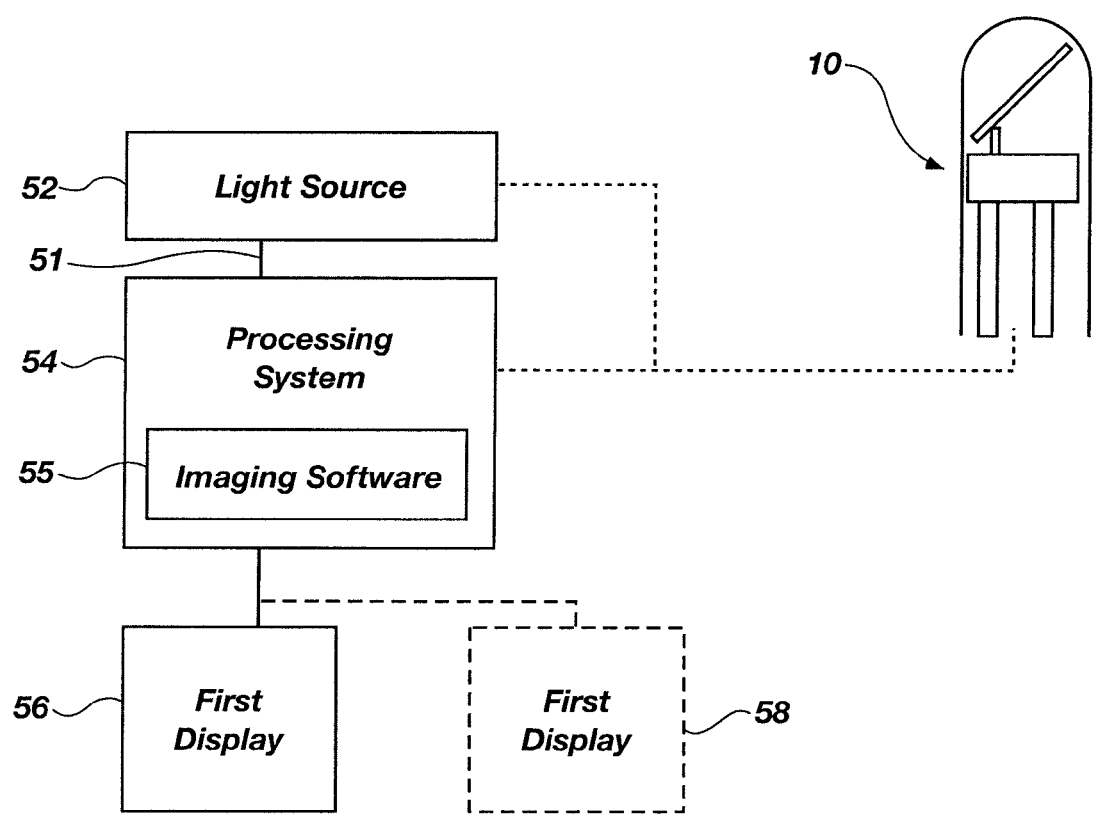
FIG. 6 is a process flow chart illustrating one embodiment of the present invention with multiple displays.

Referring now to FIGS. 5 and 6, when multiple beam portions or multiple beams of reflected illumination are recorded by the SSID, the images can be filtered and separated by a processing system 54, having imaging software 55 for processing and displaying these images on separated display screens 56 and 58, representing the various directional views. The proximal end of the elongated mini-scope body 18 can be coupled to a light source 52 or plurality of light sources, for transmitting a beam or beams of optical energy down the flexible optical conductor 20. The light source(s) can include a light-emitting diode (LED), laser, or other suitable source. The SSID can be in communication with the processing system 54, as described above. The processing system can control the light source or plurality of light sources, as represented in the figure by communication line 51.

According to another embodiment of the present invention, the light source 52 can alternatively transmit a first beam of optical energy, having a first predefined optical characteristic, for a predetermined amount of time. The light source can then transmit a second beam of optical energy, having a second predefined optical characteristic, for a predetermined amount of time (e.g., as shown in FIGS. 2a and 2b). For example, the selective mirror can be a dichroic mirror configured to reflect blue light. The light source can alternatively transmit blue followed by red light. The blue light can be reflected by the dichroic mirror and the red light can be passed through the dichroic mirror. The reflected illumination of these alternating light beams can be recorded by the SSID and communicated to the processing system 54. The imaging software 55 of the processing system can display the images recorded during the approximate time that the red light was transmitted on a first display screen 56, and the images recorded during the approximate time that the blue light was transmitted on a second display screen 58. In this manner the first display screen will display a front view from the distal end of the mini-scope 10, while the second display screen will display a lateral view from the distal end of the mini-scope. If the predetermined amount of time for alternatively transmitting a first beam is substantially short, such as approximately 0.050 seconds, the images displayed on the first and second displays will appear nearly continuous to the human eye. When multiple selective mirrors 12 are included with the mini-scope, multiple beams of light can be alternatively transmitted, recorded, processed, and displayed to show multiple directional views from the distal end of the mini-scope.

According to another embodiment of the present invention, a plurality of beams of optical energy, each having a distinct optical characteristic, can be transmitted and recorded simultaneously, as previously mentioned. Imaging software 55 of a processing system 54 can then selectively filter and display the recorded image according to the predefined characteristics of the plurality of beams of optical energy. Thus it can display multiple directional views of the distal end of the mini-scope 10 on multiple displays 56 and 58.

Figure 7:
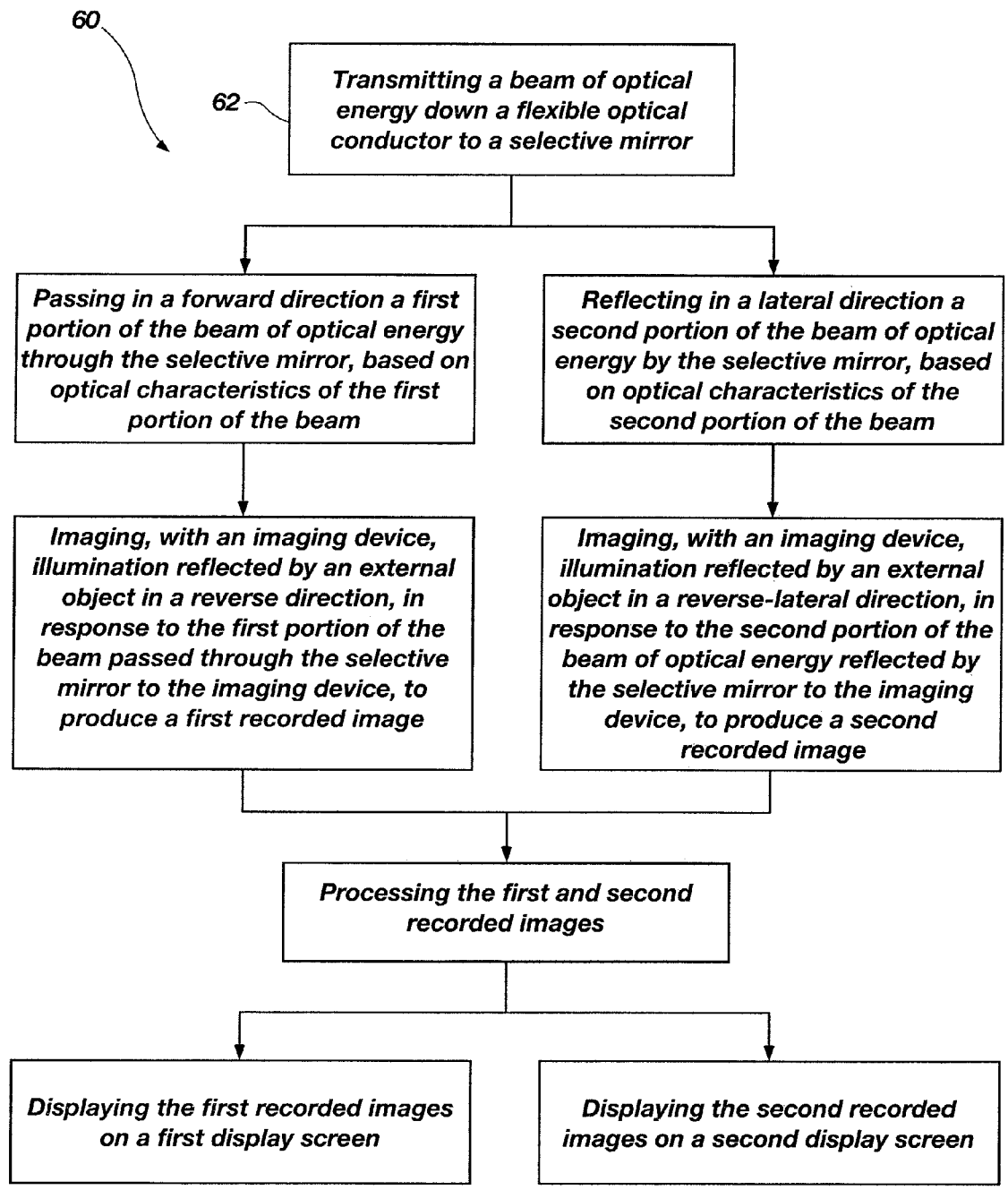
FIG. 7 is a flow chart of a method for multidirectional imaging, in accordance with another embodiment of the present invention.

As illustrated in FIG. 7, a method 60, according to one embodiment of the present invention, for multi-directional imaging with a mini-scope includes the step 62 of transmitting a beam of optical energy down a flexible optical conductor to a selective mirror. A first portion of the beam of optical energy is passed in a forward direction through the selective mirror, while a second portion of the beam is concurrently reflected by the selective mirror, based on optical characteristics of the beam. The illumination reflected by an external object in response to the first and second portions of the beam is then imaged with an imaging device to produce first and second images. These images are then processed by the processing system having imaging software. The imaging software can be configured to selectively filter the images based on various optical characteristics, including frequency characteristics. The processed images are then displayed on first and second display screens.

The first and second portions of the beam can be transmitted alternatively, sequentially, or simultaneously, or in any combination of these. The first and second portions can further include a plurality of other beams, each having varied intensities. Because the beam can be passed through the selective mirror either simultaneously or alternatively with a second beam, it will be understood that the step of passing and the step of reflection can be performed simultaneously or sequentially.

Summarizing and reiterating to some extent, benefits of the present invention include a mini-scope with multi-directional imaging functionality. Various embodiments of the mini-scope are suitable for use with different types of medical and other applications. The multi-directional imaging is achieved by positioning a means for selectively directing a beam of optical energy in the optical path of the optical energy emitted by the elongated mini-scope body. This allows light to be directed and recorded from a forward and an angled direction, or multiple angled directions. This function can reduce the need for rotation of the mini-scope and bulky and/or complex directional devices.

While the foregoing examples are illustrative of the principles of the present invention in one or more particular applications, it will be apparent to those of ordinary skill in the art that numerous modifications in form, usage, and details of implementation can be made without the exercise of inventive faculty, and without departing from the principles and concepts of the invention. Accordingly, it is not intended that the invention be limited, except as by the claims set forth below.

What is claimed is:

1. A mini-scope for multi-directional imaging, comprising:
an elongated body having a distal end and a proximal end;
means for propagating a single beam of optical energy from the distal end of the elongate body;
at least two selective mirrors disposed at the distal end of the elongated body and along an optical path of the beam, the mirrors being configured to selectively and differentially pass and reflect different portions of the beam of optical energy based on optical characteristics of the beam of optical energy, wherein the at least two selective mirrors are configured transverse to one another; and
a solid state imaging device adapted to image illumination reflected by an external object from the beam of optical energy, the illumination having passed through or reflected from one of the at least two selective mirrors to the solid state imaging device.

2. The mini-scope of claim 1, wherein at least one of the selective mirrors is a dichroic mirror.

3. The mini-scope of claim 1, wherein the optical characteristics of the beam include frequency characteristics.

4. The mini-scope of claim 1, wherein at least one of the selective mirrors is a polarizing beam splitter plate.

5. The mini-scope of claim 4, further comprising a flexible optical conductor which comprises a polarization maintaining optical fiber.

6. The mini-scope of claim 4, wherein the polarizing beam splitter plate further comprises:
   a one-way mirror portion, having opposing reflecting and nonreflecting faces, configured to pass or reflect the illumination towards the solid state imaging device, based on directional characteristics of the illumination.

7. The mini-scope of claim 1, wherein the optical characteristics of the beam include polarization characteristics.

8. The mini-scope of claim 1, wherein the at least two selective mirrors are configured to reflect different portions of the beam of optical energy in at least two different directions, based on the optical characteristics of the beam.

9. The mini-scope of claim 1 further comprising a rotating device coupled to the selective mirror.

10. The mini-scope of claim 1, further comprising:
   at least one light source disposed at the proximal end of the elongated mini-scope body for transmitting the beam of optical energy down a flexible optical conductor;
   a processing system, in communication with the solid state imaging device, having imaging software for processing and displaying images recorded by the solid state imaging device; and
   at least one display for displaying the images recorded by the solid state imaging device.

11. The mini-scope of claim 10, wherein the at least one light source is configured to alternately transmit a first beam of optical energy having a first predefined optical characteristic and a second beam of optical energy having a second predefined optical characteristic, wherein the second predefined optical characteristic is different from the first predefined optical characteristic and wherein the imaging software is configured to display images illuminated with the first beam of optical energy on a first display and display images illuminated with the second beam of optical energy on a second display.

12. The mini-scope of claim 10, wherein the at least one light source is configured to simultaneously transmit a first beam of optical energy having a first predefined optical characteristic and a second beam of optical energy having a second predefined optical characteristic, wherein the second predefined optical characteristic is different from the first predefined optical characteristic.

13. The mini-scope of claim 12, wherein the imaging software is configured to selectively filter and display images illuminated with the first beam of optical energy on a first display and images illuminated with the second beam of optical energy on a second display.

14. A mini-scope having multi-directional imaging capabilities, comprising
   means for optically conducting a beam of optical energy, said means having a distal end and a proximal end;
   means for propagating the beam of optical energy from the distal end of the means for optically conducting;
   at least two selective mirrors disposed at the distal end of the mini-scope and along an optical path of the beam of optical energy, the mirrors being configured to selectively and differentially pass and reflect the beam of optical energy based on optical characteristics of the beam of optical energy, wherein the at least two selective mirrors are configured transverse to one another; and
   means for imaging optical energy reflected from the target, said means disposed about the distal end of the mini-scope.

15. The mini-scope of claim 14, wherein the select mirrors are chosen from the group consisting of a dichroic mirror, a polarizing beam splitter plate, a polarizing beam cube, and a prism.

16. The mini-scope of claim 14, further comprising:
   at least one light source disposed at the proximal end of the means for optically conducting the beam of optical energy;
   a processing system, in communication with the means for imaging, having imaging software for processing and displaying images recorded by the means for imaging; and
   at least one display for displaying the images recorded by the means for imaging.

* * * * *